(12) United States Patent
Lin et al.

(10) Patent No.: US 7,262,858 B2
(45) Date of Patent: Aug. 28, 2007

(54) APPARATUS AND METHOD FOR ACCESSING AND PROCESSING REFLECTION IMAGE FROM MICROWELL-PLATE-BASED BIOCHIP

(75) Inventors: Chia-Po Lin, Keelung (TW); Chien-An Chen, Hsinchu (TW); Meng-Yu Chen, Miao Li County (TW); Ming-Yuan Huang, Taipei Hsien (TW); Han-Wei Wang, Taichung (TW); Chia-Hsuan Pai, Kaohsiung County (TW)

(73) Assignee: Dr. Chip Biotechnology Incorporation, Chu-nan, Miao-Li County (TW)

( * ) Notice: Subject to any disclaimer, the term of this patent is extended or adjusted under 35 U.S.C. 154(b) by 531 days.

(21) Appl. No.: 10/776,537

(22) Filed: Feb. 12, 2004

(65) Prior Publication Data

US 2004/0160607 A1    Aug. 19, 2004

(30) Foreign Application Priority Data

Feb. 14, 2003  (EP)  .................................. 03003407
Oct. 21, 2003  (TW) ............................... 92129190 A (51) Int. Cl.
*G01N 21/01* (2006.01)
*G01N 21/55* (2006.01)
*G06K 9/00* (2006.01)
*B01L 3/00* (2006.01)

(52) U.S. Cl. ...................... 356/445; 356/244; 382/133; 422/63; 422/67; 436/165
(58) Field of Classification Search ................ 356/445, 356/244, 246, 440, 399; 382/128, 133, 318; 250/576

See application file for complete search history.

(56) References Cited

U.S. PATENT DOCUMENTS

| 4,710,031 | A  | * | 12/1987 | Kelly et al. .................. 356/440 |
| 6,159,425 | A  | * | 12/2000 | Edwards et al. ............... 422/63 |
| 6,258,326 | B1 | * | 7/2001  | Modlin ....................... 422/102 |
| 6,345,115 | B1 | * | 2/2002  | Ramm et al. ................ 382/133 |
| 6,377,342 | B1 | * | 4/2002  | Coeurveille .................. 356/244 |

OTHER PUBLICATIONS

Peck et al., "Application of Enzyme Colorimetry for cDNA Microarray Detection," BioChip Technology, eds. Jing Cheng & Larry J. Kricka, Harwood Academic Publishers, pp. 325-340, 2001.

* cited by examiner

*Primary Examiner*—Roy M. Punnoose
(74) *Attorney, Agent, or Firm*—Birch, Stewart, Kolasch & Birch, LLP (57) ABSTRACT

An apparatus accesses and processes reflection images detected from microarray biochips with sidewalls. The apparatus uses a movable system to carry an optical module and a microtiter plate to achieve relative movement in different directions, so that pattern images of all wells in the microtiter plate can be retrieved during a single scanning process. Scanned image data are further compared with pre-defined patterns by a computer program for analysis.

14 Claims, 10 Drawing Sheets

APPARATUS AND METHOD FOR ACCESSING AND PROCESSING REFLECTION IMAGE FROM MICROWELL-PLATE-BASED BIOCHIP

This Nonprovisional application claims priority under 35 U.S.C. §119(a) on Patent Application No(s). 92129190 and 03003407.8 filed in TAIWAN, R.O.C. AND EUROPE on Oct. 21, 2003 and Feb. 14, 2003, the entire contents of which are hereby incorporated by reference.

BACKGROUND OF THE INVENTION

1. Field of Invention

The present invention relates to image detection and analysis of microarray biochips, and more particularly to an apparatus and a method of retrieving and analyzing colorimetric microarray images from a microtitre plate.

2. Related Art

A biochip or microarray technology has been widely used in multi-test examination. Commercial microarray application packages for microorganism or gene tests are now available. The biochip generates a lot of information after operation. Thus it needs a biochip information detecting and analysis system that simultaneously retrieves a lot of biochip information to achieve a bulk information analysis. Most of the currently available microarray biochips are developed based on glass slides as the carriers. Nucleic acids or proteins are spotted in matrix on the glass slide as probes to detect biological characteristics in unknown samples. Glass-slide-based microarray technology usually uses a fluorescent substance as detection labels to detect any information from the glass slide. As described above, the prior art, such as a confocal laser scanner made by Axon Co. or GSI Co., is exclusively used for detection of the fluorescent signals on the glass slides.

Only one single specimen can be analyzed at a time on one single glass-slide-based microarray biochip, although multiple analytes within that specimen can be analyzed simultaneously with that biochip. This is disadvantageous to bulk on-site or clinical examination of screening purpose. The microarray biochips become popular in bulk examination because of the advantage that test of a plurality of substances to be analyzed can be performed at one time, which is also useful in various fields. The microarrays that used to be placed on the glass slides are placed in the wells on a microarray carrier such like microtitre plate. The microtitre plate is a dished container having plural (at least two) wells. Microtitre plate-based biochips are a microtitre plate with plurality of wells in bottoms of which are placed in the microarray biochips. One example of the microtitre plate is a well-known 96-well ELISA microtitre plate.

There are commercially available apparatuses used to detecting and analyzing the biochips on the microtitre plate, i.e., microarray signals of 96 samples. The detecting and analyzing apparatus are for example those made by Apibio, Pierce, Spendlove Research Foundation and High Throughput Genomics Inc. All those apparatuses cannot process colorimetric signals. Those apparatuses only detect microarray signals generated by illumination, such as fluorescent signals or chemiluminescent signals.

Colorimetric technology is less expensive than the technology using a fluorescent substance. Colorimetric technology has been applied in "flat" microarrays—one type of microarrays that microarray probes are spotted on a blotting membrane made of nylon or nitrocellulose that is soft like a paper. Data on such flat color arrays are usually retrieved by a business scanner and stored as an image file that is then analyzed by an analysis program ("Application of Enzyme Colorimetry for cDNA Microarray Detection", Konan Peck and Yuh-Pyng Sher, in BioChip Technology, eds. Jing Cheng & Larry J. Kricka, Harwood Academic Publishers, 325-340, 2001). The membrane usually has a considerably large size such as 20 cm*10 cm, which occupies a lot of memory space. Furthermore, the membrane cannot allow bulk examination.

Figure 9:
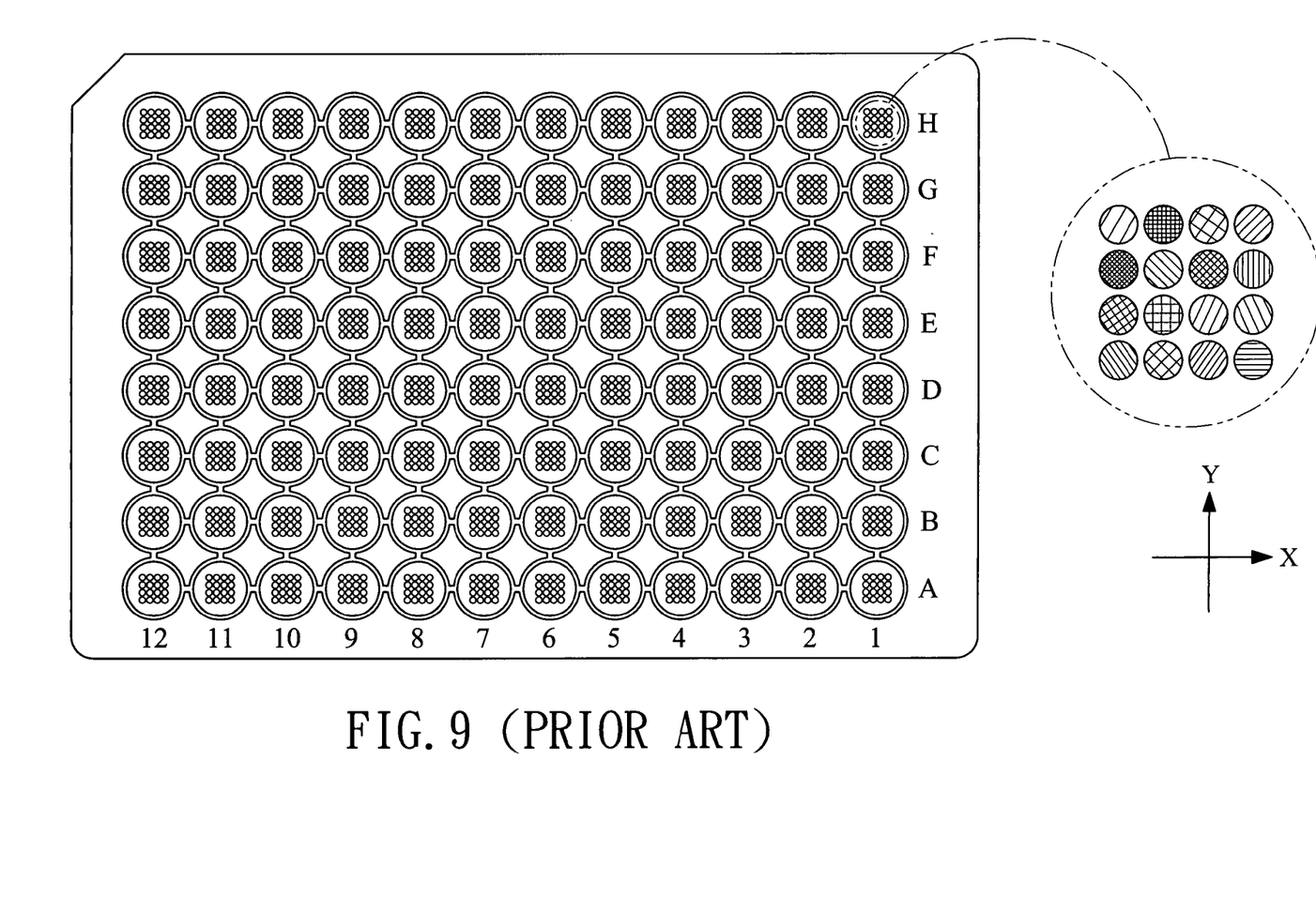
FIG. 9 is a top view of a conventional 96-well ELISA microtitre plate.
Figure 10:
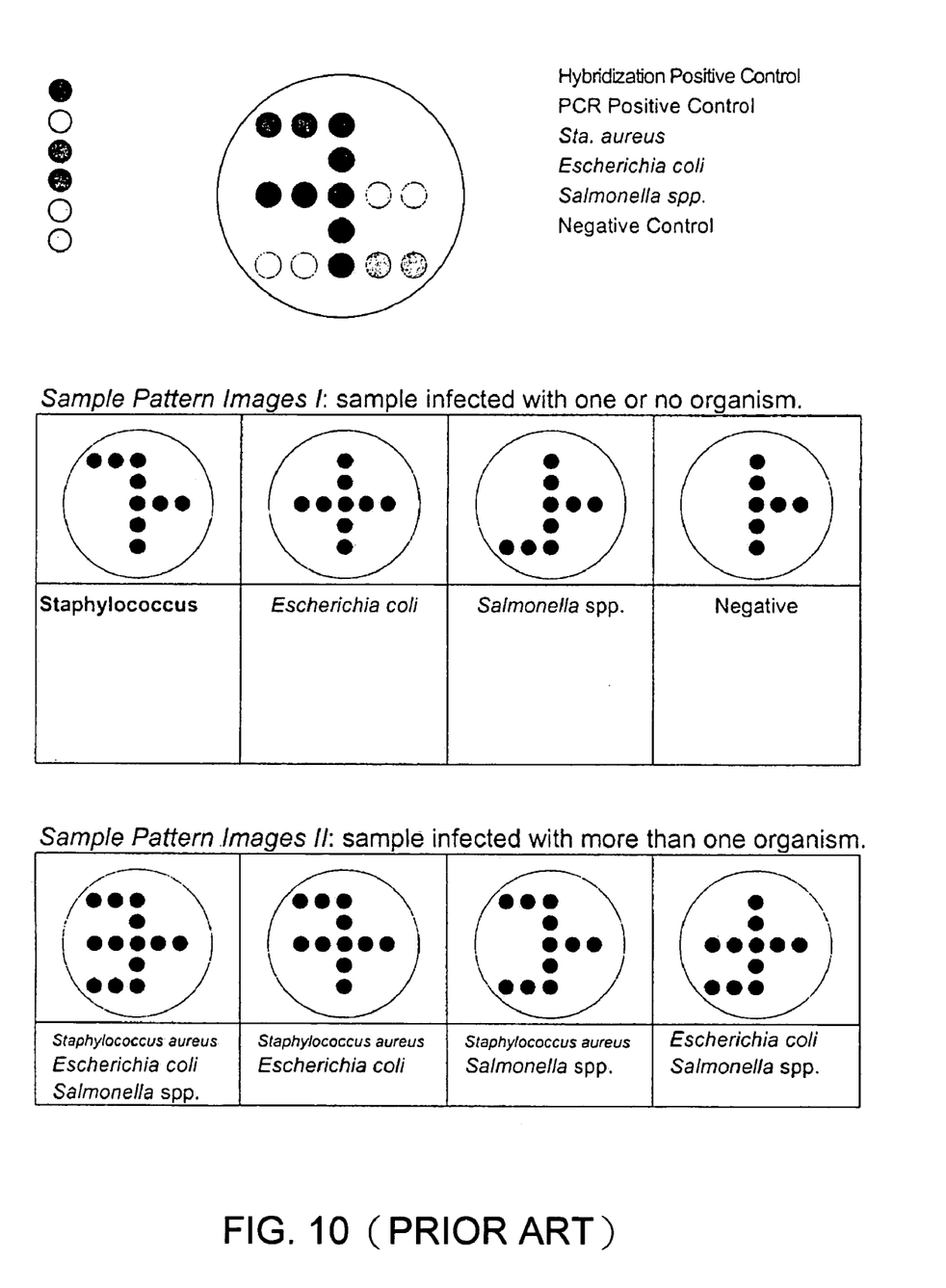
FIG. 10 is a legend list of each image pattern in microarray biochips known in the art.

In terms of cost and bulk screening, there is a great demand for a colorimetric analysis of microarray biochips. FIG. 9 is a schematic view of a 96-well white scintillation micro plate as a carrier of a plural number of microarrays. A single set of microarray is placed in bottom of each well for single-sample examination. If the microtitre plate has 96 wells, then 96 samples are to be tested at one time. Meanwhile, a chromatic matrix result is generated. For example, nucleic acid probes on one set of microarrays serve to examine whether in one single food sample exist one or more of pathogenic germs such as *Staphylococcus aureus*, *Escherichia coli*, and the like. As indicated by circles in an upper portion of FIG. 10, a set of nucleic acid probes of 5×5-dot matrix is placed in each well of the 96-well microtitre plate. After reaction, only one of 8 possible colorimetric dot patterns is obtained for one well, as shown in a lower portion of FIG. 10. If all of the 96 wells undergo the reaction at the same time, it is not easy to recognize all the dot patterns of 96 wells visually, and thus the performance of bulk examination is greatly reduced. Therefore, it requires an image detection apparatus to massively process the chromatic microarray data.

However, the currently available technology retrieves the images of wells of the whole microtitre plate in sequence, which takes a long time and needs a lot of memory space for such great processing load.

The microarray biochips are mounted in the wells with sidewalls of a certain height. Such microarrays with certain thickness make the image acquisition from ordinary business scanner harder. The colorimetric signals in the microarrays on blotting membranes are located on a flat surface without any sidewall so that light uniformly distributes over and reflects by the flat surface without any concern of image brightness and uniformity. While the wells of the 96-well microtitre plate have a depth-diameter ratio of about 1.6 or more, which may cause light to be partially blocked by a part of the sidewall of the well. Non-uniform light distribution over the wells results in poor image quality. If common business scanner is used to scan the 96-well microtitre plate to retrieve the colorimetric signals in the microarrays, either the target dots cannot be focused or the single light source provided by the scanner cannot uniformly radiate over the wells to clearly retrieve the microarray images. In other words, common business scanner cannot be used in colorimetric images retrieving from deep-well microarrays.

Therefore, there is a need of a detection apparatus exclusively for detecting reflection images from microarray biochips, which can be applied in bulk examination of microarrays.

SUMMARY OF THE INVENTION

The objects of the invention are to provide an image detection apparatus that overcomes the following prior disadvantages: the non-uniform luminosity in the wells of the microtitre plate, slow image detection speed, and image deformation due to large image scanning area.

In order to achieve the above and other objectives, the image detection apparatus for biochips on the microtitre plate according to the invention includes a carrier, an optical module, and a movable system. The carrier is used to carry the biochips of microtitre plate with microarray signals inside each well. The optical module includes at least one white light source, a set of reflective lenses, a linear CCD and a focusing lens. The white light source irradiates light on the biochips on the carrier. The reflective lenses adjust a light path reflected from the biochips. The CCD receives the reflected light from the biochips to retrieve images in microarrays. The movable system carries the carrier and the optical module to achieve relative movement in a first direction and/or a second direction so that all the biochips are scanned.

A computer program is further provided to perform comparison of the scanned images with pre-defined patterns. All image data are sequentially picked up. All dots constituting the microarrays in the image data are found. The dots are compared with features of microarrays and previously stored in a database. Then, the comparison result is produced.

The image detection and analysis process performed in the invention includes the following steps. The image detection apparatus and the carrier carrying biochips thereon are driven to move respectively in a first direction and a second direction to achieve relative movement to retrieve all images of the biochips on the carrier. The images are transformed and transmitted to a computer, to be compared with the pre-defined patterns.

The invention provides the following advantages.

1. Light sources used in the invention allow uniform light distribution over wells of the microtitre plate. Therefore, image contrast and signal intensity obtained from light reflection are improved.

2. Light sources used in the invention irradiate light over the whole microtitre plate such as a 96-well ELISA microtitre plate. Therefore, data of the samples in the microtitre plate can be processed at the same time.

3. The process of the invention performs double scanning, overcoming the prior problems such as image distortion.

4. The double scanning technique used in the invention greatly reduces the dot matrix data size and the image retrieving time.

BRIEF DESCRIPTION OF THE DRAWINGS

The present invention will become more fully understood from the detailed description given herein below illustration only, and is thus not limitative of the present invention, wherein.

DETAILED DESCRIPTION OF THE INVENTION

FIG. 1 through FIG. 6 are exploded views illustrating an image detection apparatus according to one embodiment of the invention.

Figure 1:
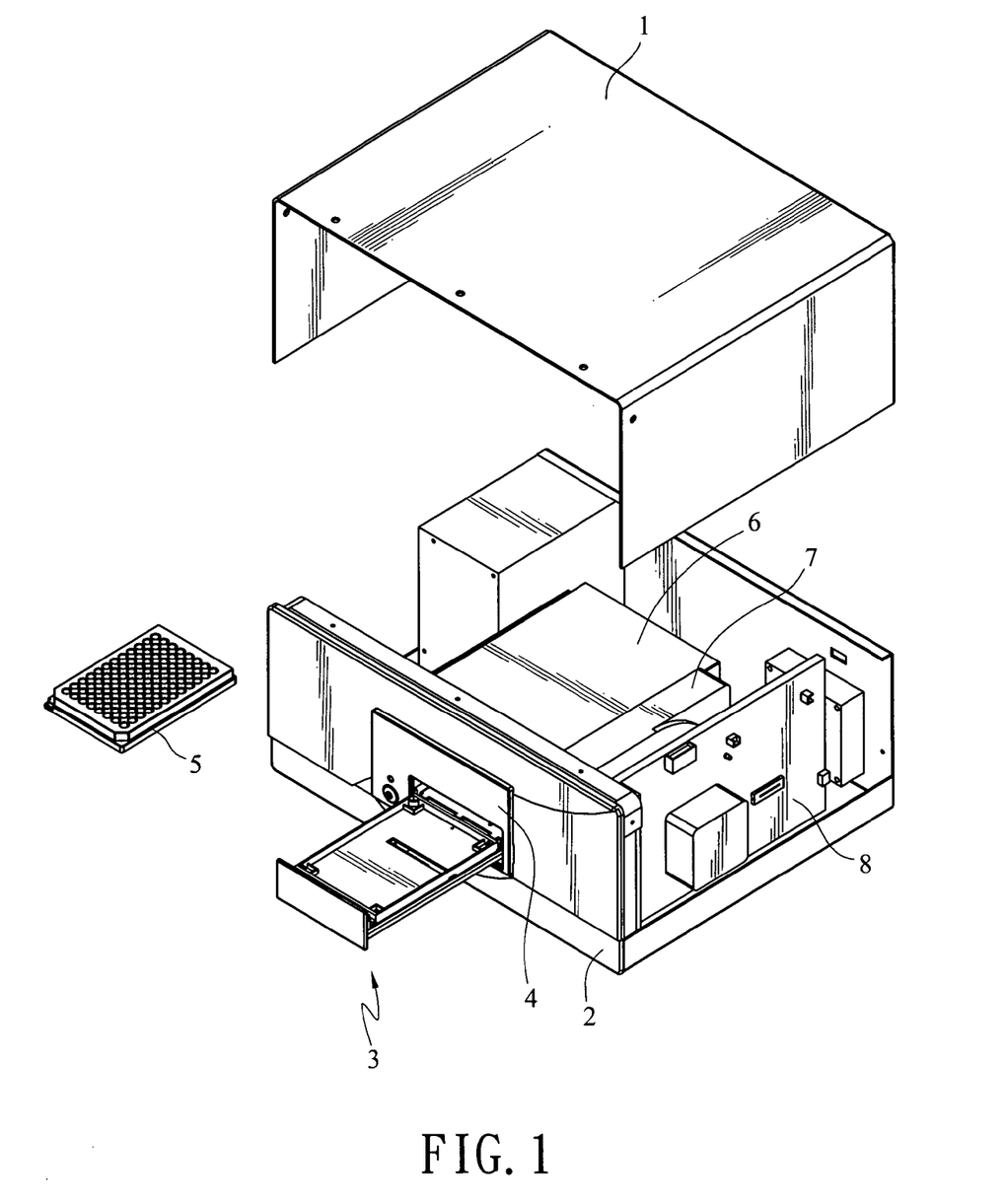
FIG. 1 is an exploded view of an image detection apparatus after the casing is detached from the receptacle according to one embodiment of the invention.

FIG. 1 is an exploded view of an image detection apparatus after a casing is detached from a receptacle 2 according to one embodiment of the invention. An opening is formed at a front side of the base for receiving a slidable tray set 3 that can be pushed into or pulled out from the receptacle 2. An ornamental plate 4 is mounted at an outer periphery of the opening for labeling or visual aesthetics. An end user can place a microtitre plate 5 that has undergone experimental tests into the pulled out tray set 3. Then, the tray set 3 is pushed back under the control of a computer program to process sequential image reading.

Figure 2:
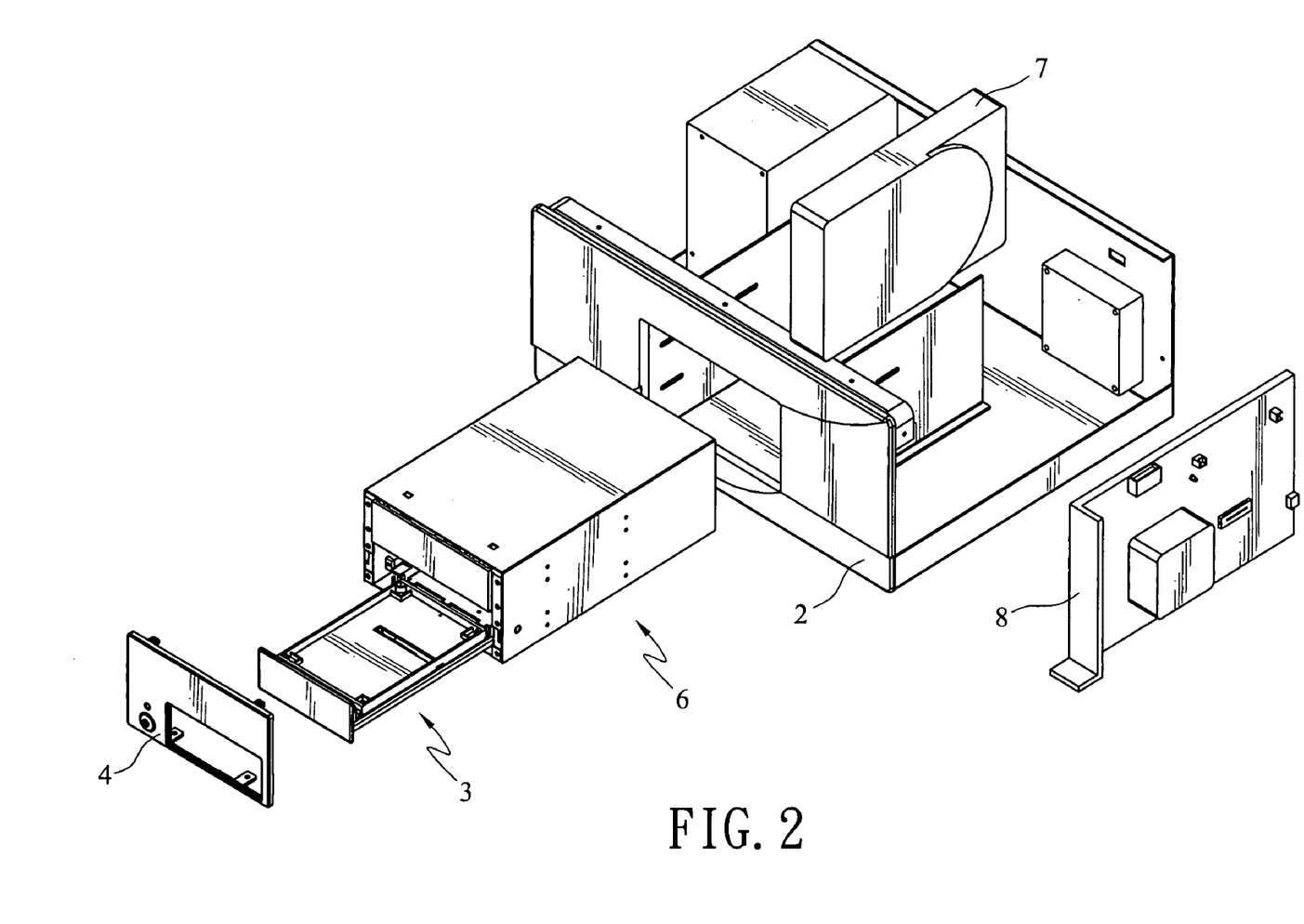
FIG. 2 is another exploded view of the embodiment of FIG. 1.

FIG. 2 is another exploded view of the embodiment illustrated in FIG. 1. The receptacle 2 includes a core module 6, a hard disk 7 and a circuit board 8 that are arranged in parallel inside the receptacle 2. The tray set 3 is included inside the core module 6.

Figure 3:
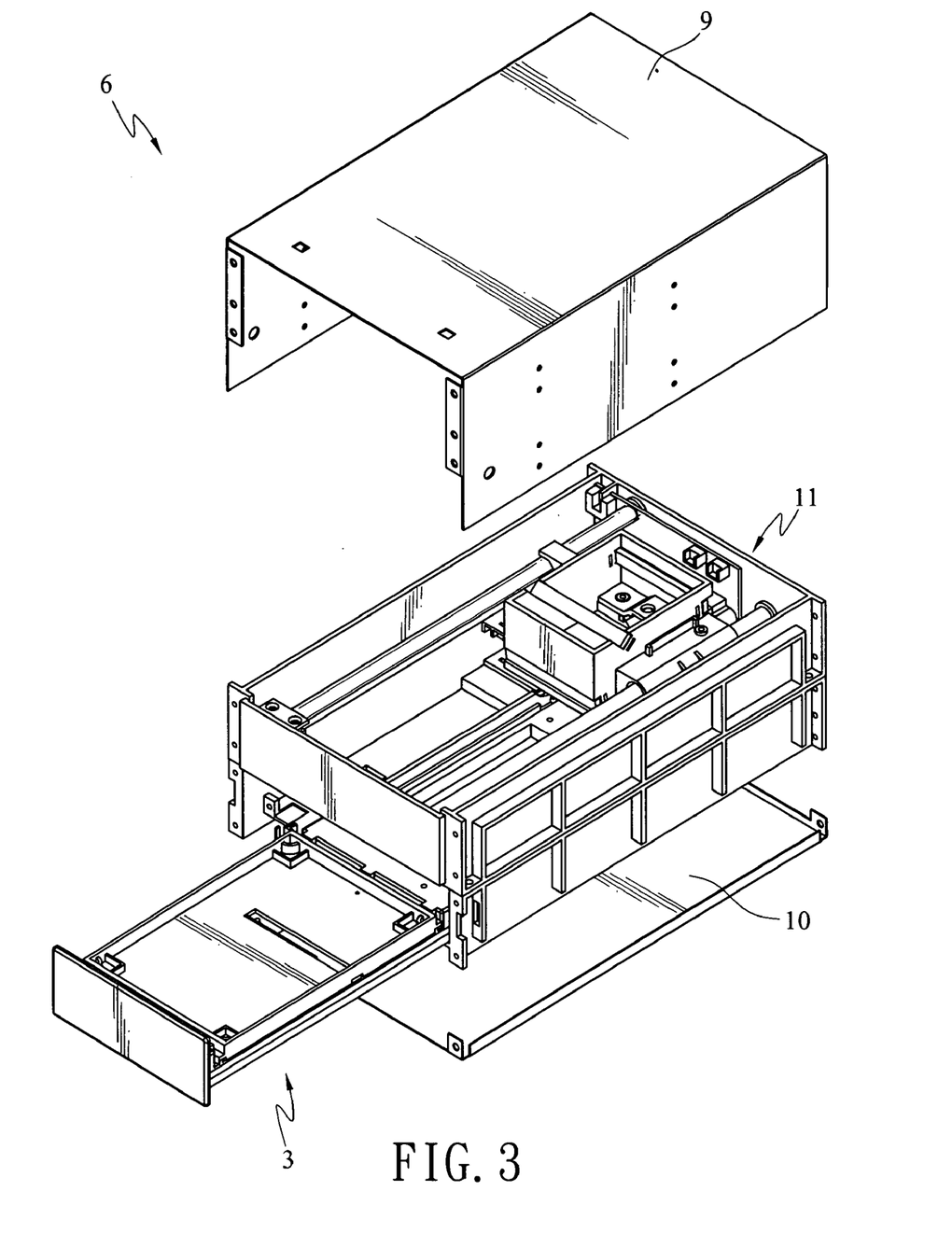
FIG. 3 is an exploded view of a core module according to one embodiment of the invention.

FIG. 3 is an exploded view of the core module 6. The core module 6 includes a lid 9, a base 10 and an image-scanning module 11. The lid 9 and the base 10 define an accommodating space in which the image-scanning module 11 is mounted.

Figure 4:
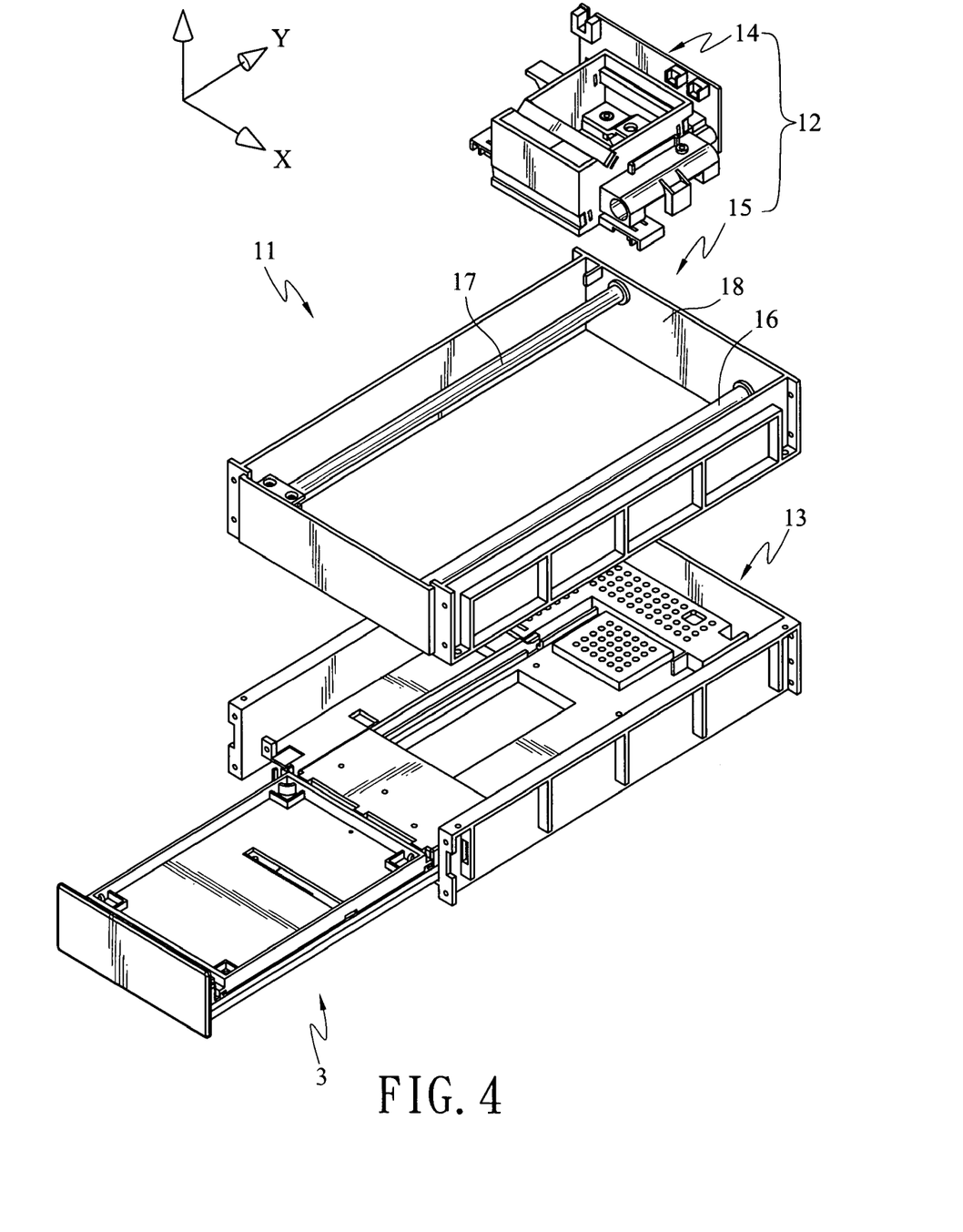
FIG. 4 is an exploded view of an image-scanning module according to one embodiment of the invention.

FIG. 4 is an exploded view of the image-scanning module 11. It is noted that sub-zone scanning is achieved via X-Y axis relative movements between a linear CCD of an optical module 14 and the microtitre plate 5. The image-scanning module 11 includes an optical sub-module 12 at an upper part and a tray sub-module 13 at a lower part. The optical sub-module 12 includes the optical module 14 and a sliding rail module 15. The sliding rail module 15 includes slide rails 16, 17 along which the optical module 14 slides, and a rail frame 18. In order to retrieve images at well bottoms of the microtitre plate 5, the optical sub-module 12 drives the optical module 14 to move forth and back in a Y direction, as shown in FIG. 4. Two sides of the optical module 14 movably mount on the sliding rails 16, 17. The optical module 14 slides along the sliding rails 16, 17 between two opposite ends of the frame 18 via a gear set (not shown) mounted on an inner side of the frame 18.

Figure 5:
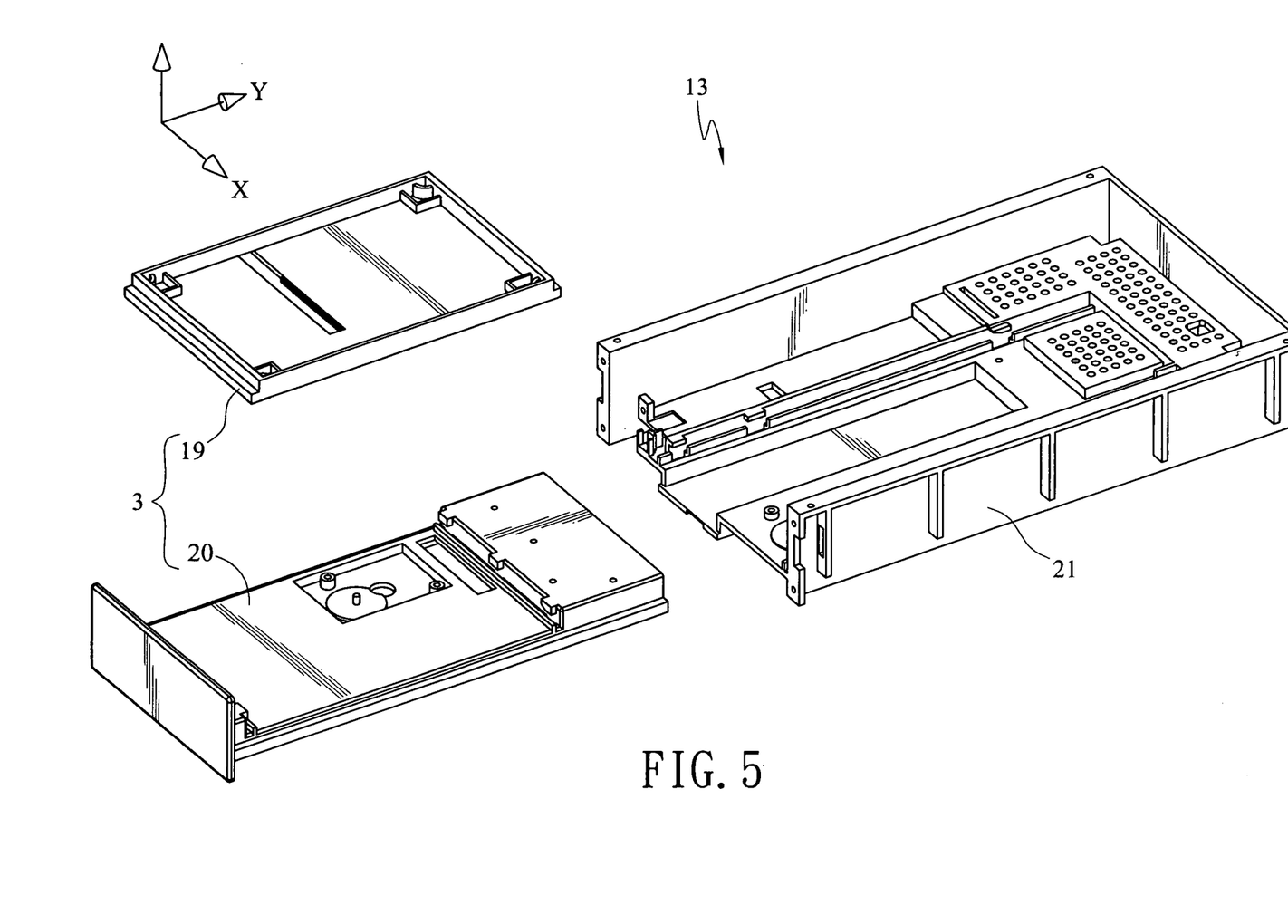
FIG. 5 is an exploded view of a tray sub-module according to one embodiment of the invention.

FIG. 5 is an exploded view of the tray sub-module 13. The tray sub-module 13 allows convenient access of the microtitre plate, and scanning across a predetermined area of the microtitre plate in an X direction vertical to the linear CCD of the optical module 14. The tray sub-module 13 includes a tray 19, a drawer 20 and a cartridge 21. The tray 19 is mounted on the drawer 20 to form a tray set 3 that is pulled out or pushed into the cartridge 21 in the Y direction.

After the microtitre plate 5 is placed on the tray 19 and pushed back to the cartridge 21, reading analysis is performed. The moveable tray set 3 moves into the cartridge 21 along the Y direction.

The microtitre plate 5 to be analyzed is placed on the tray 19 and then pushed into the cartridge 21 for reading analysis. The movable tray set 3 moves relative to the stationary cartridge 21 from the front side to the inner side of the image detection apparatus. The tray set 3, like a drawer, can be pulled out from the front side of the cartridge 21 and completely pushed into the cartridge 21.

When the tray set 3 is pushed into the cartridge 21, the tray 19 carrying the microtitre plate 5 can be driven to move in an X direction by a motor (not shown) located under the drawer 20. The drawer 20 is stationary, like the cartridge 21. The range of movement of the tray 19 along the X direction inside the cartridge 21 is equal to an inner width of the cartridge 21.

Figure 6:
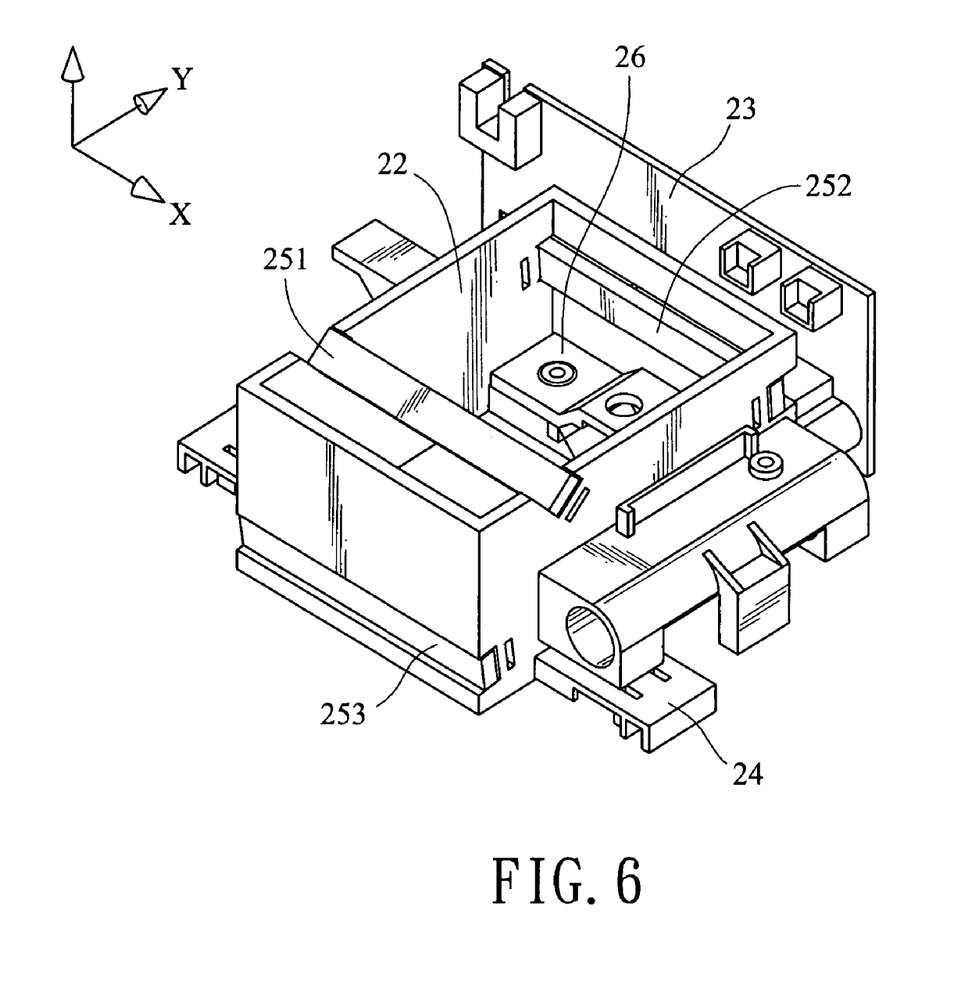
FIG. 6 is an enlarged view of an optical module according to one embodiment of the invention.

FIG. 6 is an enlarged view of the optical module 14. The optical module 14 includes a control circuit board 23 mounted at a rear side of a housing 22 of the optical module 14. The optical module 14 moves along the Y direction of the sliding rail module 15. Two parallel projection lamps are mounted under the optical module 22. In contrast to the prior art where a fluorescent reflected image is generated using a light source at a specific wavelength, the projection lamps 24 generate a set of uniform white light sources suitable for the colorimetric technology used in biochips. The white light sources irradiate on the microtitre plate 5. A series of visible light images of microtitre plate generated by reflection of light from the projection lamps 24 is reflected via lenses 251, 252, 253 mounted in the housing 22 (see FIG. 7a and description hereafter). The image is then focused on a linear CCD 26 in the housing 22 via a focus lens 254 (not shown, but is mounted between the lens 253 and the CCD 26) and received by the linear CCD.

The image detection apparatus of the invention can uniformly light each well via at least a white light source properly arranged. The image detection apparatus includes a movable system (such as the optical module 14 and the tray sub-module 13) for carrying and moving the carrier (such as a microtitre plate 5) having microarray biochips thereon, at least a white light source (such as the projection lamps 24), a set of reflecting mirrors (such as lenses 251, 252, 253), at least a focus lens (such as focus lens 254), and a linear CCD (such as the CCD 26).

The light source used in the invention can be arranged in the following manners.

Figure 7A:
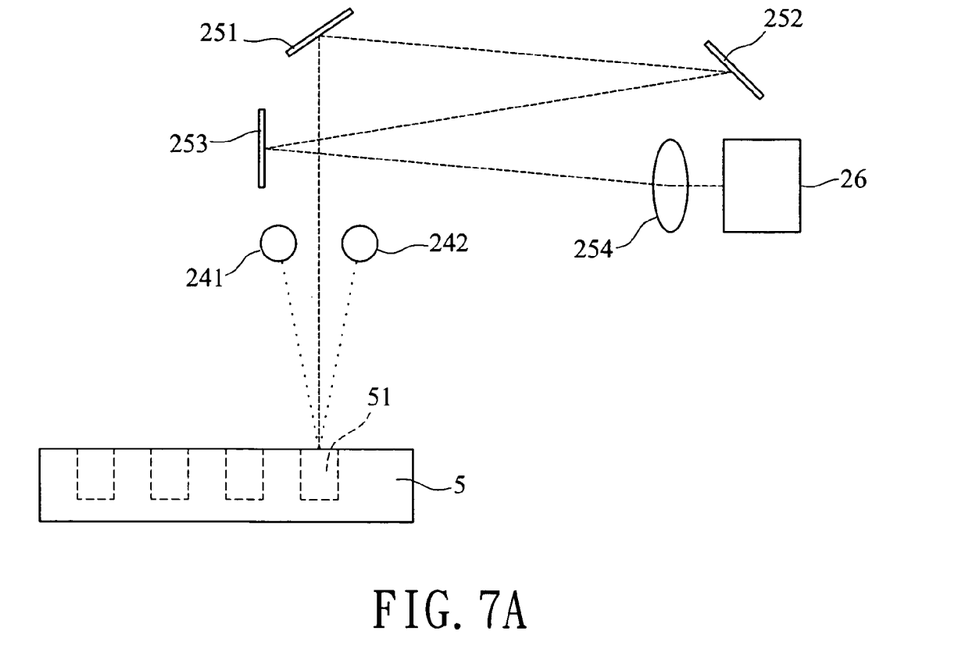
FIG. 7A and FIG. 7B are schematic views showing two arrangements of the image detection apparatus according to one embodiment of the invention.

One arrangement of the light source is shown in FIG. 7A. Two linear white light sources 241, 242 are arranged under the lens 251 and above wells 51 of the microtitre plate 5. The white light sources 241, 242 alternately irradiate on the wells 51 of the microtitre plate 5 so that parts of the wells where light is slightly blocked can be complemented to render the light intensity inside the wells uniformly. The image of the microtitre plate 5 generated by the reflected visible light is guided to the focus lens 254 subsequently via the lens 251, the lens 252 (referred to as a reflective mirror) and the lens 253 (referred to as a reflective mirror 253) and then focused to the CCD 26. The image scanning is completed.

Figure 7B:
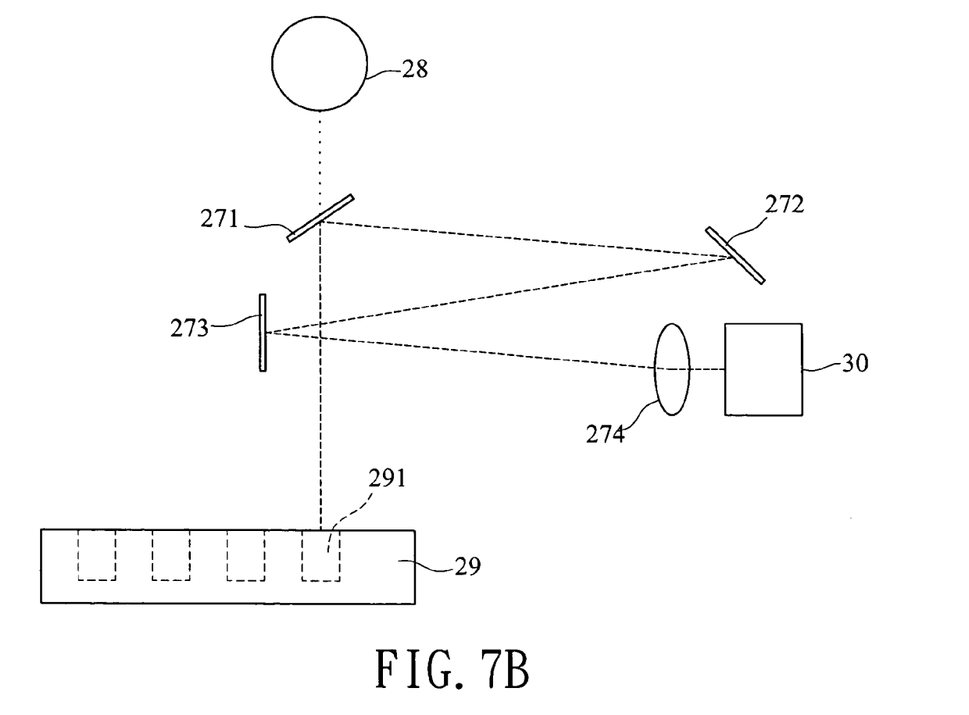

Another alternative arrangement of the light source is shown in FIG. 7B. A white light source 28 is mounted at a right rear of a lens 271 (referred to as a dichroic mirror). The white light source 271 has a diameter larger than the lens 271. Therefore, light comes out from a peripheral portion of the white light source uncovered by the lens 271 to form a circular light source that uniformly irradiates down to each well 291 of a microtitre plate 29. The image of the microtitre plate 29 generated by the reflected visible light is directed to the lens 272 (the reflective mirror) via the lens 271, guided to the lens 273 (the reflective mirror) and then focused to a CCD 30 via the focus lens 274.

The well fit for this invention has various shapes such as square or circle.

The linear CCD retrieving the reflected image in a microarray occupies less memory space compared to the block type CCD used in a microscope. Further, it is difficult to perform a continuous integration of the image retrieved by the block type CCD, which is not favorable to the analysis of a large-area image. In contrast, the CCD in the invention is suspended on the movable element (such as the optical module 14) to simultaneously retrieve the images and move along one horizontal direction. Then, integration is performed to obtain all the images from the microtitre plate 5.

If the image detection process performed by the CCD is not correct, a periphery of the image may be deformed, which adversely affects subsequent reading. Therefore, optimization is performed before image detection.

Referring to FIG. 9 for plate reading orientation, the linear CCD first scans A1 to D1 wells of a 96-well microtitre plate. Then, the linear CCD travels in an A2-D2 direction and keeps going in sequence until it reaches an area in an A12-D12 direction. Then, by moving the tray, the linear CCD starts in an E12-H12 direction and ends in an E11-H11 direction. The whole microtitre plate is scanned twice, and each time scans in 4-well width. Therefore, moving the CCD back and forth for one time is enough to complete scanning of the 96-well microtitre plate. In order to meet the requirement of the above process, the linear CCD overall moves along 2 directions in respect of the microtitre plate.

In other words, in the image detection system, the lens set and the CCD are preferably mounted on one movable element (such as the optical module 14) moving along one or two directions. If the movable element moves along one direction, then the linear CCD retrieves the image of the microtitre plate from the beginning of a first region (wells A1-D1) to the end of the first region (wells A12-D12). After the image detection of the first region is completed, the linear CCD moves along the other direction relative to the microtitre plate to retrieve the image from the second region in a direction opposite to that of the first region. Thereby, the image detection of a first half portion of the microtitre plate is completed.

Figure 8:
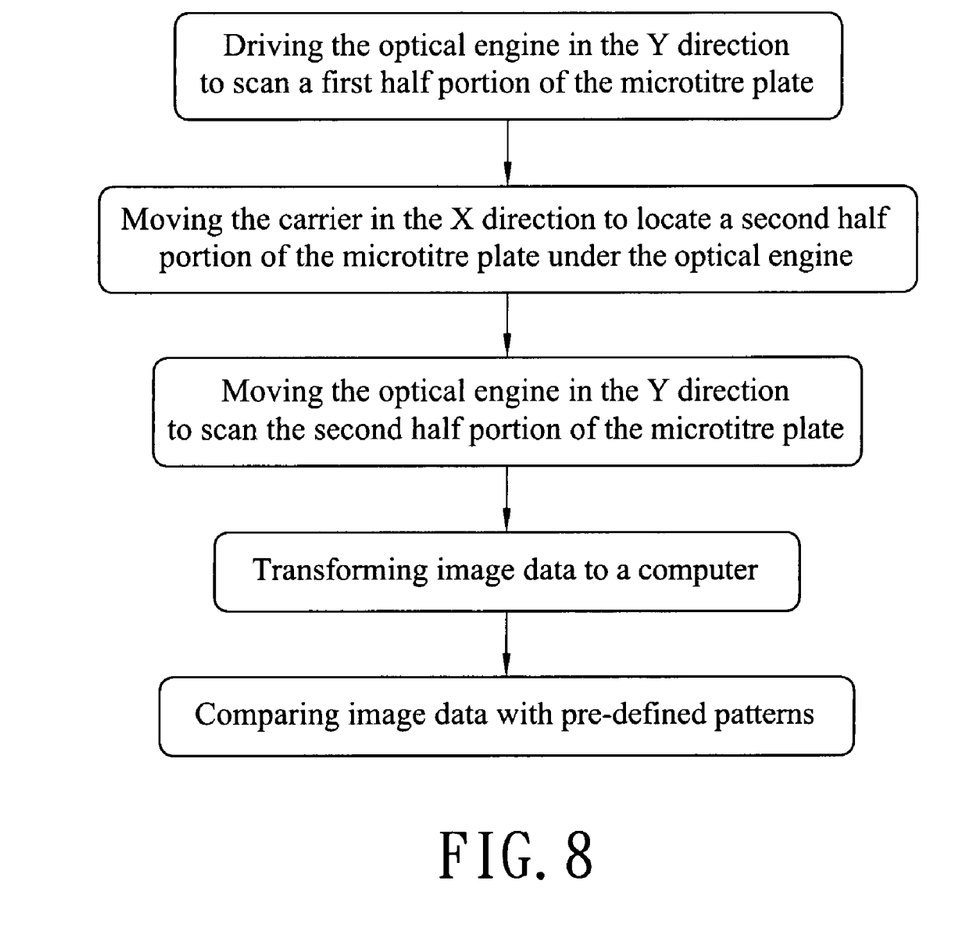
FIG. 8 is a flow chart of an image detection process according to one embodiment of the invention.

Then, the movable element moves from the wells A12-D12 to the wells E12-H12 in the X direction. The X-axis movement of the movable element is conducted in the direction opposite to the first half portion of the microtitre plate. Meanwhile, when the movable element completes one X-axis movement, it moves to the next column in the Y direction back to the initial position. Thereby, the image detection of a second half portion of the microtitre plate is completed, and a new microtitre plate can be processed. FIG. 8 illustrates an image scanning process according to the invention.

Although the CCD is used as a movable element, other components of the image detection apparatus can be configured in a movable or stationary manner, as long as the relative movement between the CCD and the microtitre plate can be achieved. For example, the microtitre plate is movable while the CCD is stationary. Alternatively, both the CCD and microtitre plate can be movable. It should be understood that other embodiments could include images being retrieved by relatively moving samples and the image detection apparatus.

The shape of the microtitre plate is not particularly limited, as long as wells are formed therein. The number of the wells is not particularly limited either. For example, 3-, 24-, 96-well plate or plate with more wells can apply to the invention.

A computer program can be further provided for analyzing the retrieved images. The computer program includes coding means, stored in a computer readable medium, to compare scanned images with pre-defined patterns.

Most currently available software applications are designed for monitoring different gene representing groups. They mainly operate to find out dots and compare spectrum intensities of different colors at the same dot. In this invention, the software application is used to define sample characteristics related to pathogens by recognizing specific patterns in the microarray. Standard patterns can be predetermined or defined by the user. The position of the array and dots in critical number can be confirmed. After pattern reorganization, the result is analyzed by a built-in analysis tool and produced in the form of a table.

Specifically, the computer program performs comparison in the following steps. All image data are sequentially picked up. All dots constituting the microarrays in the image data are found. The dots are compared with features of microarrays previously stored in a database. Then, the comparison result is generated. Preset default data in the database are as follows:

1. Basic conditions:
1.1 matrix size
1.2 dot size
1.3 dot signal and background
2. Microarray condition:
2.1 dot pattern
2.2 dot name at particular position
2.3 feature of the whole array As described above, the image detection apparatus for biochips on the microtitre plate according to the invention includes the following elements. (1) A carrier used to carry the microtitre plate of microarrays. (2) An optical module, including the white light source, the reflective lenses, the linear CCD and the focus lens. The white light source irradiates on the biochips put on the carrier. The reflective lenses adjust the light paths of light reflected from the biochips. The CCD receives the reflected light from the biochips to retrieve images in microarrays. (3) A movable system, carrying the above carrier and the optical module to perform relative movement in a first and/or second direction so that all the biochips are scanned.

The image detection apparatus for biochips on the microtitre plate according to the invention can work with a computer program to compare the scanned images with pre-defined patterns.

The image detection process according to the invention, as shown in FIG. 8, drives the optical module to scan a first half portion of the microtitre plate in the Y direction. The carrier moves in the X direction to locate a second half portion of the microtitre plate under the optical module. Then, the optical module moves in the Y direction to scan the second half portion of the microtitre plate. The scanned images are transformed to the computer, to be compared with pre-defined patterns.

The image detection apparatus of the invention can retrieve images of chips of any specifications. The scanning direction is limited to orthogonal X and Y directions. The scanning sequence can be varied according to the specification of the microtitre plate, or according to the movable system selected.

For example, in contrast to FIG. 8, the carrier may move in the first direction. Meanwhile, the linear CCD starts to sequentially retrieve images of the biochip on a first half portion of the carrier. Then, the optical module moves in the second direction to a second half portion of the carrier. Thereafter, the carrier moves in a direction opposite to the first direction. The linear CCD sequentially retrieves images of the biochip on a second half portion of the carrier. Finally, the optical module moves in a direction opposite to the second direction back to its initial position.

Alternatively, one of the carriers and the optical module are fixed while the other moves in the first and second directions.

The image detection and analysis process performed in the invention includes the following steps. The image detection apparatus and the carrier carrying biochips therein are driven to move respectively in a first and second direction to achieve relative movement and retrieve all images of the biochips on the carrier. The images are transformed and transmitted to the computer and compared with pre-defined patterns.

The invention disclosed above will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus detecting reflection images from microarray biochip with sidewall, comprising:
a carrier, carrying a plurality of microarray biochips;
an optical module, scanning the biochips; and
a movable system, carrying the carrier and the optical module respectively to achieve relative movement so that all the biochips are scanned, if the carrier is moveable in a first direction, then the optical module being movable in a second direction, if the optical module is moveable in the first direction, then the carrier being movable in the second direction, if the carrier is movable in both the first and the second directions, then the optical module being at a stationary condition, if the optical module is moveable in both the first and the second directions, then the carrier being at a stationary condition;
wherein the optical module comprising:
at least a white light source, irradiating on the biochips;
at least a reflective lens, adjusting a light path of a reflected light from the biochips;
at least a linear CCD (Charge Coupled Device), receiving the reflected light to retrieve images from the biochips; and
at least a focus lens, focusing the reflected light to the CCD.

2. The apparatus of claim 1, wherein the optical module further comprises a dichroic mirror located between the white light source and the biochips.

3. The apparatus of claim 1, wherein the carrier is for carrying a microtitre plate having a plurality of wells with sidewalls, the shape of each of the wells is circle or square.

4. The apparatus of claim 3, wherein the number of wells is 3, 24 or 96.

5. The apparatus of claim 1, wherein the movable system comprises a sliding rail module and a tray sub-module for respectively carrying the optical module and the carrier.

6. The apparatus of claim 5, wherein the sliding rail module further comprises at least a sliding rail, a rail frame, and a belt/gear set.

7. The apparatus of claim 5, wherein the tray sub-module further comprises a tray, a drawer and a cartridge.

8. The apparatus of claim 1 further comprising a computer program used to compare the image data with pre-defined patterns.

9. A method of retrieving and analyzing reflection images from microarray biochips, comprising the steps of:
    moving an optical module and a carrier carrying a plurality of biochips thereon respectively, if the carrier is moveable in a first direction, then the optical module being movable in a second direction, if the optical module is moveable in the first direction, then the carrier being movable in the second direction, if the carrier is movable in both the first and the second directions, then the optical module being at a stationary condition, if the optical module is moveable in both the first and the second directions, then the carrier being at a stationary condition, to achieve relative movement and retrieve images data from all the biochips, the optical module having a linear CCD(Charge Coupled Device) and a white light source;
    transforming the image data to a computer; and
    comparing the image data with a plurality of pre-defined patterns previously stored in a database; and
    outputting a comparison result.

10. The method of claim 9, wherein one of the optical module and the carrier moves in the first direction, the other one of the optical module and the carrier which does not move in the first direction moves in the second direction.

11. The method of claim 10, wherein the optical module and the carrier move relatively via the steps comprising:
    a) the optical module moving in the first direction, meanwhile the linear CCD retrieving images from the biochips on a first half portion of the carrier;
    b) the carrier moving in the second direction to reach a second half portion of the carrier;
    c) the optical module moving in a direction opposite to the first direction in step a), meanwhile the linear CCD retrieving images from the biochips on a second half portion of the carrier; and
    d) the carrier moving in a direction opposite to the second direction in step b) to reach its initial position.

12. The method of claim 10, wherein the optical module and the carrier move relatively via the steps comprising:
    a) the carrier moving in the first direction, meanwhile the linear CCD retrieving images from the biochips on a first half portion of the carrier;
    b) the optical module moving in the second direction to reach a second half portion of the carrier;
    c) the carrier moving in a direction opposite to the first direction in step a), meanwhile the linear CCD retrieving images from the biochips on a second half portion of the carrier; and
    d) the optical module moving in a direction opposite to the second direction in step b) to reach its initial position.

13. The method of claim 9, wherein one of the carrier and the optical module is fixed, and the other moves in the first and the second directions, the relative movement of the optical module and the carrier comprising the steps of:
    a) the optical module and the carrier moving relatively to each other in the first direction, meanwhile the linear CCD retrieving images from the biochips on a first half portion of the carrier;
    b) the optical module and the carrier moving relatively to each other in the second direction so that the optical module reaches a second portion of the carrier;
    c) the optical module and the carrier moving relatively in a direction opposite to the first direction in step a), meanwhile the linear CCD retrieving images from the biochips on the second portion of the carrier; and
    d) the optical module and the carrier moving relatively to each other in a direction opposite to the second direction in step b) to reach their initial position.

14. The method of claim 9, wherein the comparing step of the image data is performed steps via a computer program comprising the steps of:
    retrieving the image data from the biochips sequentially;
    finding a plurality of dots constituting microarrays in the image data; and
    comparing the dots with the patterns having pre-defined features and stored in the database.

* * * * *